(12) United States Patent
Ryan (10) Patent No.: US 7,699,846 B2
(45) Date of Patent: Apr. 20, 2010

(54) SURGICAL INSTRUMENT AND METHOD

(75) Inventor: Phillip A. Ryan, Memphis, TN (US)

(73) Assignee: Gyrus ENT L.L.C., Bartlett, TN (US)

( * ) Notice: Subject to any disclaimer, the term of this patent is extended or adjusted under 35 U.S.C. 154(b) by 1056 days.

(21) Appl. No.: 11/353,031

(22) Filed: Feb. 14, 2006

(65) Prior Publication Data

US 2006/0264927 A1    Nov. 23, 2006

Related U.S. Application Data

(60) Provisional application No. 60/658,147, filed on Mar. 4, 2005.

(51) Int. Cl.
*A61B 18/18* (2006.01)

(52) U.S. Cl. .............. 606/50; 606/45; 606/48; 606/170; 606/171; 606/177

(58) Field of Classification Search ............ 606/41, 606/45, 50, 167, 169, 170, 171, 176, 178, 606/179
See application file for complete search history.

(56) References Cited

U.S. PATENT DOCUMENTS

| | | | | |
|---|---|---|---|---|
| 3,557,780 | A * | 1/1971 | Sato | 600/141 |
| 4,646,738 | A * | 3/1987 | Trott | 606/170 |
| 5,376,078 | A * | 12/1994 | Dinger et al. | 606/170 |
| 5,437,630 | A * | 8/1995 | Daniel et al. | 604/22 |
| 5,601,586 | A * | 2/1997 | Fucci et al. | 606/180 |
| 5,665,101 | A * | 9/1997 | Becker et al. | 606/180 |
| 5,669,926 | A | 9/1997 | Aust et al. | |
| 5,690,660 | A * | 11/1997 | Kauker et al. | 606/180 |
| 5,904,681 | A | 5/1999 | West, Jr. | |
| 5,922,003 | A * | 7/1999 | Anctil et al. | 606/170 |
| 6,193,715 | B1 * | 2/2001 | Wrublewski et al. | 606/45 |
| 6,251,120 | B1 * | 6/2001 | Dorn | 606/170 |

(Continued)

FOREIGN PATENT DOCUMENTS

EP    0623317    11/1994

*Primary Examiner*—Linda C Dvorak
*Assistant Examiner*—Amanda Scott
(74) *Attorney, Agent, or Firm*—Oliff & Berridge, PLC (57) ABSTRACT

A surgical instrument comprises a hollow tube (18) having a cutting window (16) at the distal end portion. An inner tube (15) is disposed within the tube (18) and is mounted for rotation about its longitudinal axis. A cutting tool (17) is located at the distal end of the tube (15), and is positioned adjacent to the cutting window (16). An outer tube (14) is provided over the tube (18). A motor (5) is provided for rotating the inner tube (15), and saline is fed to the cutting window (16) via a passageway (25) between the tubes (15) and (18). The inner tube (15) has a central lumen (24) through which tissue cut by the cutting tool (17) is removed under the action of a source of suction (12). The outer surface of the tube (18) is covered with an electrically insulating layer (22) and coagulating RF signals are supplied between the tube (18) and the outer tube (14) so as to coagulate tissue at the cutting window (16). A weakened portion (43) of the outer tube (14) ensures that when the outer tube (14) and hollow tube (18) are bent to form a curved portion (42), the relative positioning of the respective distal ends of the tubes (14) and (18) is maintained.

16 Claims, 7 Drawing Sheets

U.S. PATENT DOCUMENTS

| | | |
|---|---|---|
| 6,533,749 B1 * | 3/2003 | Mitusina et al. ............... 604/22 |
| 6,610,059 B1 | 8/2003 | West, Jr. |
| 7,052,494 B2 | 5/2006 | Goble et al. |
| 2003/0060862 A1 * | 3/2003 | Goble et al. ................... 607/96 |
| 2005/0070818 A1 * | 3/2005 | Mueller ....................... 600/564 |

* cited by examiner

SURGICAL INSTRUMENT AND METHOD

This application claims priority from U.S. provisional application 60/658,147 filed Mar. 4, 2005, the entire disclosure of which is herein incorporated by reference.

This invention relates to a surgical instrument, and to a system and method for removing tissue from a surgical site on or within a patient's body. In a preferred construction, the invention relates to an electrosurgical system and method that can use electrical and mechanical energy to treat tissue.

Known mechanical surgical instruments include simple scalpels which are used for cutting soft tissue, rotatable shavers which are also used for removing soft tissue, and rotatable burrs which are used for cutting harder tissue such as bone.

Known electrosurgical instruments include monopolar and bipolar devices, both of which are used primarily for treating or cauterising soft tissue. Typically tissue is removed using a mechanical cutting device such as a shaver (or by an electrosurgical device operating in cutting or vaporisation mode), and then the cauterising device is used to coagulate tissue in order to stench bleeding.

It is known to use a surgical instrument which includes a mechanical element, such as a rotary shaver or burr, and an electrosurgical instrument such as a monopolar or bipolar device. A known instrument of this type is described in U.S. Pat. No. 5,904,681, which describes an instrument having a shaver or burr rotatably mounted within an outer sleeve, and an electrosurgical electrode mounted at the end of the outer sleeve on the "back" of the instrument (i.e. opposite to the cutting window of the device).

U.S. Pat. No. 6,610,059 is a further device from the same inventor in which an electrosurgical electrode is provided on the back of a mechanical cutting device. Another prior art device is U.S. Pat. No. 6,193,715 which provides an adapter for converting a conventional mechanical cutting device such as a shaver or burr into a combined mechanical/electrosurgical instrument.

It is an object of the present invention to provide an improved surgical device, bearing in mind the limitations of the prior art devices described above.

Accordingly, there is provided a blade assembly for a surgical instrument comprising
  a) an intermediate hollow tube having a central passageway and a cutting window at a distal end thereof, the tube being substantially straight but having a portion designated for bending, the bend portion being located over a finite distance between its proximal end and the cutting window;
  b) an inner hollow tube rotatably mounted in the central passageway of the intermediate tube and providing a central suction lumen, the inner tube having a flexible portion corresponding to the bend portion of the intermediate tube;
  c) a cutting tool disposed at the distal end of the inner tube such that the cutting tool is accessible through the cutting window of the intermediate tube, the cutting tool including a cut-out defining a tissue-cutting edge;
  d) an outer tube disposed over the intermediate hollow tube and having an opening at its distal end so as to allow access to the cutting window of the intermediate tube, the outer tube having a weakened portion located between the proximal end of the tube and the distal opening therein, the weakened portion corresponding to the bend portion of the intermediate tube and being such that the inter-relationship between the opening in the outer tube and the cutting window in the intermediate tube is substantially the same whether in a first condition in which the outer tube and intermediate tube are straight, or in a second condition in which the outer tube and intermediate tube are bent at the bend portion and weakened portion respectively.

The inter-relationship between the opening in the outer tube and the cutting window in the intermediate tube includes either the spacing between the two, the relative orientation between the two, or both. In one arrangement, the intermediate and outer tubes are both electrically conducting, and there is an electrically insulating layer disposed between the intermediate and outer tubes. The electrically insulating layer is conveniently provided by means of an insulating material deposited on to the outer surface of the intermediate tube, and there are first and second contacts respectively associated with the outer and intermediate tubes for connecting the tubes to respective poles of an electrosurgical generator. In this way a coagulating radio frequency signal is supplied between the outer and intermediate tubes and hence the material surrounding the cutting window in the intermediate tube and that surrounding the opening in the outer tube. Thus the inter-relationship between the opening in the outer tube and the cutting window in the intermediate tube can be of crucial importance in ensuring a consistent and predictable tissue-coagulating effect.

According to a preferred arrangement, the intermediate and outer tubes are both electrically conducting, and there is an electrically insulating layer disposed between the intermediate and outer tubes. The electrically insulating layer is conveniently provided by means of an insulating material deposited on to the outer surface of the intermediate tube, and there are first and second contacts respectively associated with the outer and intermediate tubes for connecting the tubes to respective poles of an electrosurgical generator. In such an RF device the spacing and orientation of the distal ends of the intermediate and outer tubes is critical. The intermediate and outer tubes can be designed such that their respective spacing and orientation is accurately determined. However, when the tubes are bent after initial manufacture to form an angled blade assembly, the spacing and orientation between the distal ends of the two tubes can be disrupted. By forming a weakened portion in the outer tube to accommodate the bending of the tube, this disruption can be minimised.

In a preferred embodiment, there is also provided a source of irrigating fluid, adapted to irrigate the blade assembly. The irrigating fluid is preferably an electrically conductive fluid such as saline, and is conveniently transmitted to the cutting tool between the inner tube and the intermediate tube. The irrigating fluid not only helps to cool and clean the cutting tool, but also assists in the electrosurgical coagulation process.

The weakened portion preferably comprises a portion of the outer tubular member with one or more sections removed therefrom. According to one convenient arrangement, the weakened portion comprises a portion of the wall of the tube in the form of a strip, with the remainder of the tubular member being removed. The strip is preferably a longitudinally extending strip, and can extend either along the inside or the outside of the curve of the bend in the outer tubular member, once formed. The strip conveniently extends in the form of a parallel strip with straight sides, or alternatively in the form of a zig-zag element. According to a further alternative, the strip extends helically around the circumference of the tubular element.

Whichever form of strip is employed, the removal of one or more sections from the portion of the outer tubular member allows it to be bent without distorting the spatial positioning of the distal end. Preferably, the strip constitutes less than 50% of the circumference of the tubular member, conveniently less than 20%, and typically even less than 10% of the circumference thereof.

According to an alternative arrangement, the weakened portion comprises a portion of the tubular member in the form of a mesh, or even a plurality of ring elements connected one to another by joining members.

The invention further resides in a curved blade assembly for a surgical instrument including;
  a) an intermediate hollow tube having a central passageway and a cutting window at a distal end thereof, the tube having a bend portion, the bend portion being located over a finite distance between its proximal end and the cutting window;
  b) an inner hollow tube rotatably mounted in the central passageway of the intermediate tube and providing a central suction lumen, the inner tube having a flexible portion corresponding to the bend portion of the intermediate tube;
  c) a cutting tool disposed at the distal end of the inner tube such that the cutting tool is accessible through the cutting window of the intermediate tube, the cutting tool including a cut-out defining a tissue-cutting edge;
  d) an outer tube disposed over the intermediate hollow tube and having an opening at its distal end so as to allow access to the cutting window of the intermediate tube, the outer tube having a weakened portion located between the proximal end of the tube and the distal opening therein, the weakened portion corresponding to the bend portion of the intermediate tube and being such that the inter-relationship between the opening in the outer tube and the cutting window in the intermediate tube is substantially the same in its bent condition as it was before the bend was formed.

According to another aspect of the invention, the invention resides in a surgical system including
  i) a blade assembly comprising;
    a) an intermediate hollow tube having a central passageway and a cutting window at a distal end thereof, the tube having a bend portion, the bend portion being located over a finite distance between its proximal end and the cutting window;
    b) an inner hollow tube rotatably mounted in the central passageway of the intermediate tube and providing a central suction lumen, the inner tube having a flexible portion corresponding to the bend portion of the intermediate tube;
    c) a cutting tool disposed at the distal end of the inner tube such that the cutting tool is accessible through the cutting window of the intermediate tube, the cutting tool including a cut-out defining a tissue-cutting edge;
    d) an outer tube disposed over the intermediate hollow tube and having an opening at its distal end so as to allow access to the cutting window of the intermediate tube, the outer tube having a weakened portion located between the proximal end of the tube and the distal opening therein, the weakened portion corresponding to the bend portion of the intermediate;
    e) an electrically insulating layer disposed between the intermediate and outer tubes, the intermediate and outer tubes both being electrically conducting; and
    f) first and second contacts associated with the outer and intermediate tubes respectively for connecting the tubes to respective poles of an electrosurgical generator;
  ii) a motor adapted to rotate the inner hollow tube within the intermediate tube;
  iii) a source of suction connected to the central suction lumen of the inner hollow tube; and
  iv) an electrosurgical generator connected to the first and second contacts so as to selectively supply RF energy between the intermediate and outer tubes;

the arrangement being such that the rotation of the cutting tool is capable of causing the cutting of tissue in the region of the cutting window, while the RF energy supplied to the intermediate and outer tubes coagulates tissue in the region of the cutting window.

The invention will now be described in greater detail, by way of example, with reference to the drawings, in which.

Figure 1:
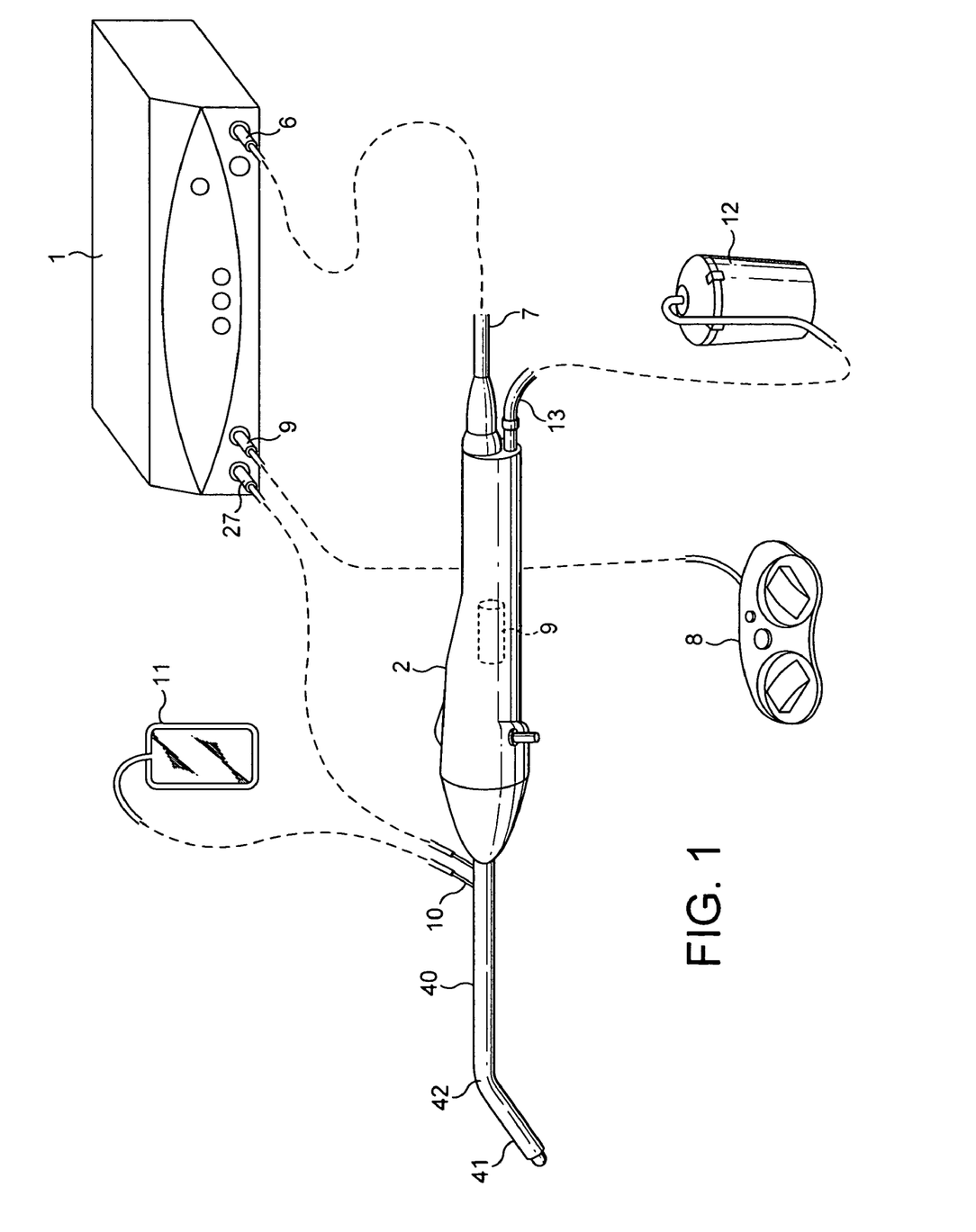
FIG. 1 is a schematic diagram of a surgical system incorporating a surgical instrument in accordance with the invention.

Referring to the drawings, FIG. 1 shows a surgical system which includes a controller/generator 1 and a handpiece 2 having a detachable surgical probe shown generally at 3. The probe includes a proximal straight portion 40, and a distal straight portion 41 separated by a curved portion 42. The probe 3 includes a rotatable inner tubular member 15, driven by a motor shown schematically at 5 within the handpiece. Power signals for the motor 5 are supplied to the handpiece 2 from an output socket 6 on the generator 1, via connector cord 7. Activation of the controller 1 may be performed by means of footswitch 8, coupled to the controller by means of connector cord 9. An inlet port 10 allows saline to be fed from a saline source 11 to the distal end of the probe 3. A source of suction 12 is also provided, coupled to the handpiece by cord 13. Cord 27 supplies electrosurgical coagulation signals from the generator 1 to the probe 3.

Figure 2:
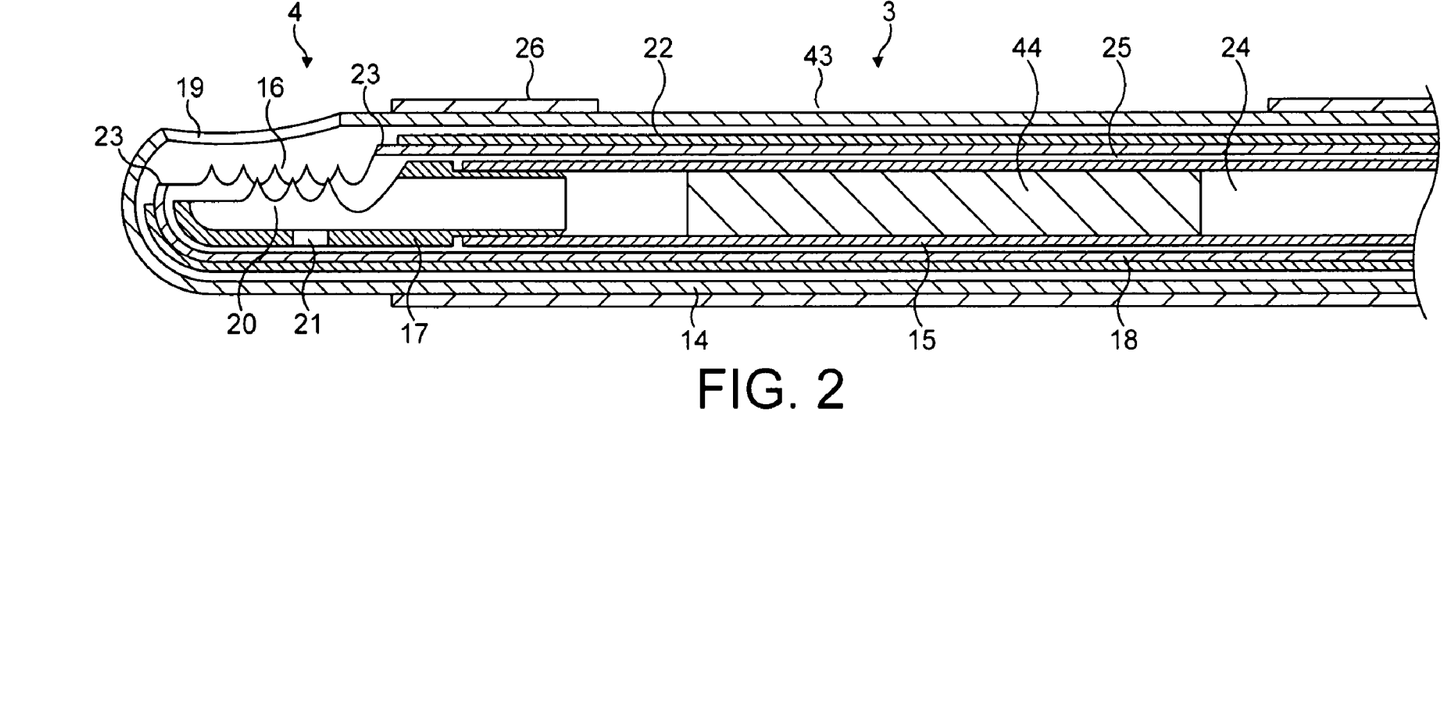
FIG. 2 is a sectional side view of the distal end of the surgical instrument of FIG. 1.

FIG. 2 shows a sectional view of the distal end 4 of the probe 3, prior to the formation of the curved portion 42. The probe 3 comprises an inner tubular member 15, an outer tubular member 14 and an intermediate tubular member 18. A cutting tool 17 is located at the distal end of the inner member 15, and can be accessed through lateral cutting windows 16 and 19 in the intermediate and outer tubular members respectively. The cutting tool includes a cut-out portion 20 having a periphery constituted by a serrated edge, and an optional suction aperture 21 located opposite the cut-out portion 20.

The tubes 14, and 18 are both formed of a conductive metallic material such as stainless steel, although the outer tubular member 14 can alternatively be formed of copper (which is better at conducting heat away from the distal end 4 of the probe 3). The intermediate tubular member 18 is coated with an electrically insulating Ethylene Chloro-trifluoroethylene (ECTFE) layer 22, the layer 22 stopping marginally short of the distal end of the tube 18 so as to leave exposed portions as shown at 23.

The outer tube 14 is provided with a weakened portion, as shown generally at 43. The weakened portion 43 is designed to become some or all of the curved portion 42, when formed. The inner tubular member 15 is formed of a non-conducting flexible polymer material, with the cutting tool 17 being formed of stainless steel. (Alternatively, the inner tube 15 can be formed of stainless steel in which case the cutting tool 17 can be formed integrally with the inner tube 15.) The inner tubular member is further provided with an additional flexible portion 44 corresponding to the weakened portion 43. The inner tubular member 15 is hollow defining a suction lumen 24, which in use is connected to the source of suction 12. A passageway 25 between the inner tubular member 15 and the intermediate member 18 is connected in use to the saline source 11, and is used to deliver saline to the distal end 4 of the probe 3. The outer member 14 is optionally covered with a heat-shrink electrically insulating sleeve 26, covering the probe 3 with the exception of the distal end 4 including the cutting window 19.

Figure 3:
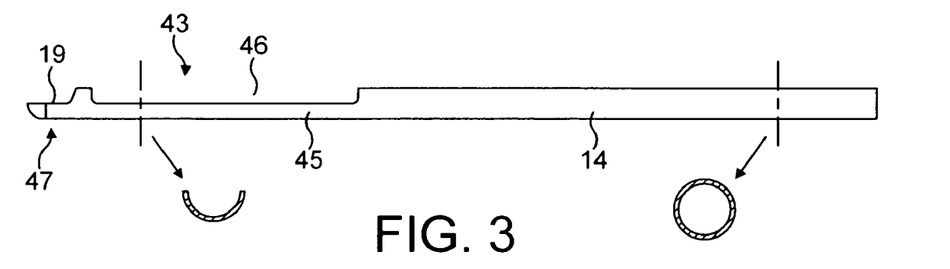
FIG. 3 is a schematic side view of one embodiment of the outer tube of the instrument of FIG. 1.

As shown in FIG. 3, the weakened portion 43 comprises a portion of the outer tubular member 14 in which a section of the circumference of the tube has been removed to leave a strip 45 and a cut-out portion 46. In FIG. 3, the strip 45 constitutes slightly less than 50% of the circumference of the tube. When the tube 14 is bent to form the curved portion 42, the weakened portion 43 ensures that the longitudinal and rotational position of the distal end 47 of the outer tube (including the window 19) is maintained.

Figure 4:
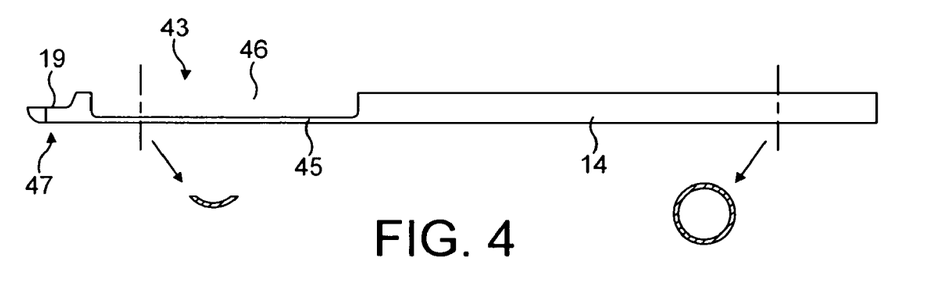
FIG. 4 is a schematic side view of an alternative embodiment of the outer tube of the instrument of FIG. 1.

FIG. 4 shows an alternative design of outer tube 14, similar to that of FIG. 3 in that it has a strip 45 and cut-out portion 46. In the embodiment of FIG. 4, the strip 45 constitutes less than 10% of the circumference of the tube 14.

Figure 5:
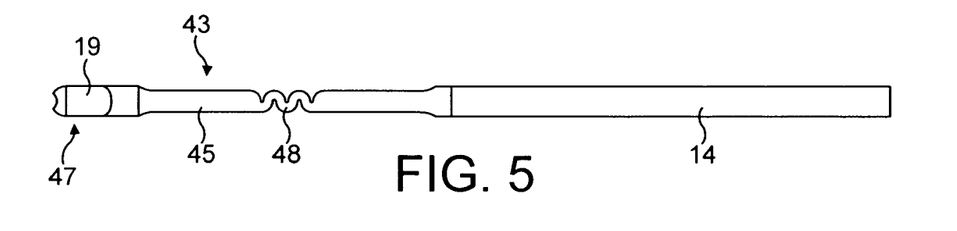
FIG. 5 is a schematic plan view of a further embodiment of the outer tube of the instrument of FIG. 1.

FIG. 5 shows a different type of embodiment in which the strip 45 is not linear as in FIGS. 3 and 4, but includes a zig-zag portion 48.

Figure 6:
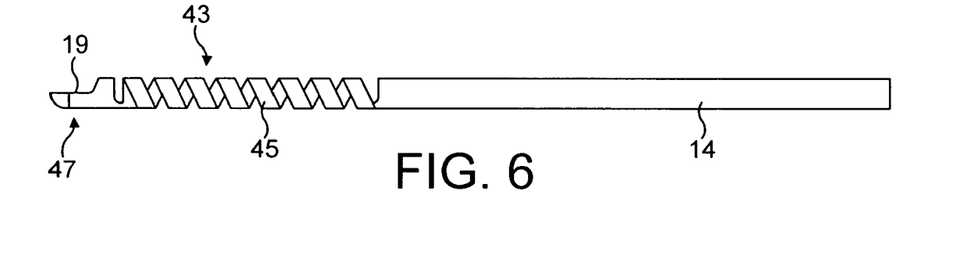
FIG. 6 is a schematic side view of a further embodiment of the outer tube of the instrument of FIG. 1.

FIG. 6 shows an embodiment in which the strip 45 extends helically around the circumference of the tube 14.

Figure 7:
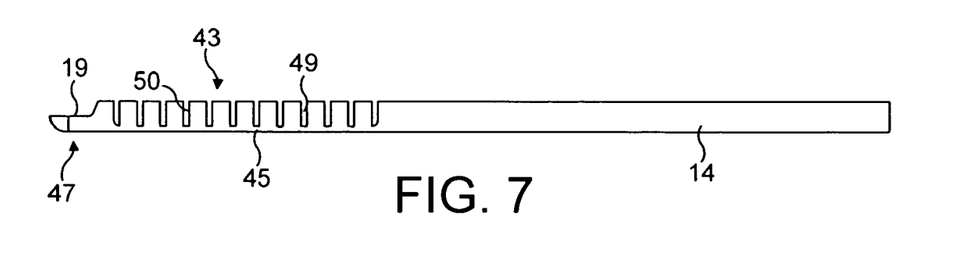
FIG. 7 is a schematic side view of a further embodiment of the outer tube of the instrument of FIG. 1.

FIG. 7 shows an embodiment in which the strip 45 additionally has ring segments 49 attached thereto, with gaps 50 therebetween. Each of the embodiments of FIGS. 3 to 7 provides a weakened portion 43 capable of accommodating the bending of the outer tube 14 while maintaining the relative spatial position of the distal end of the tube with respect to the inner components.

Figure 8:
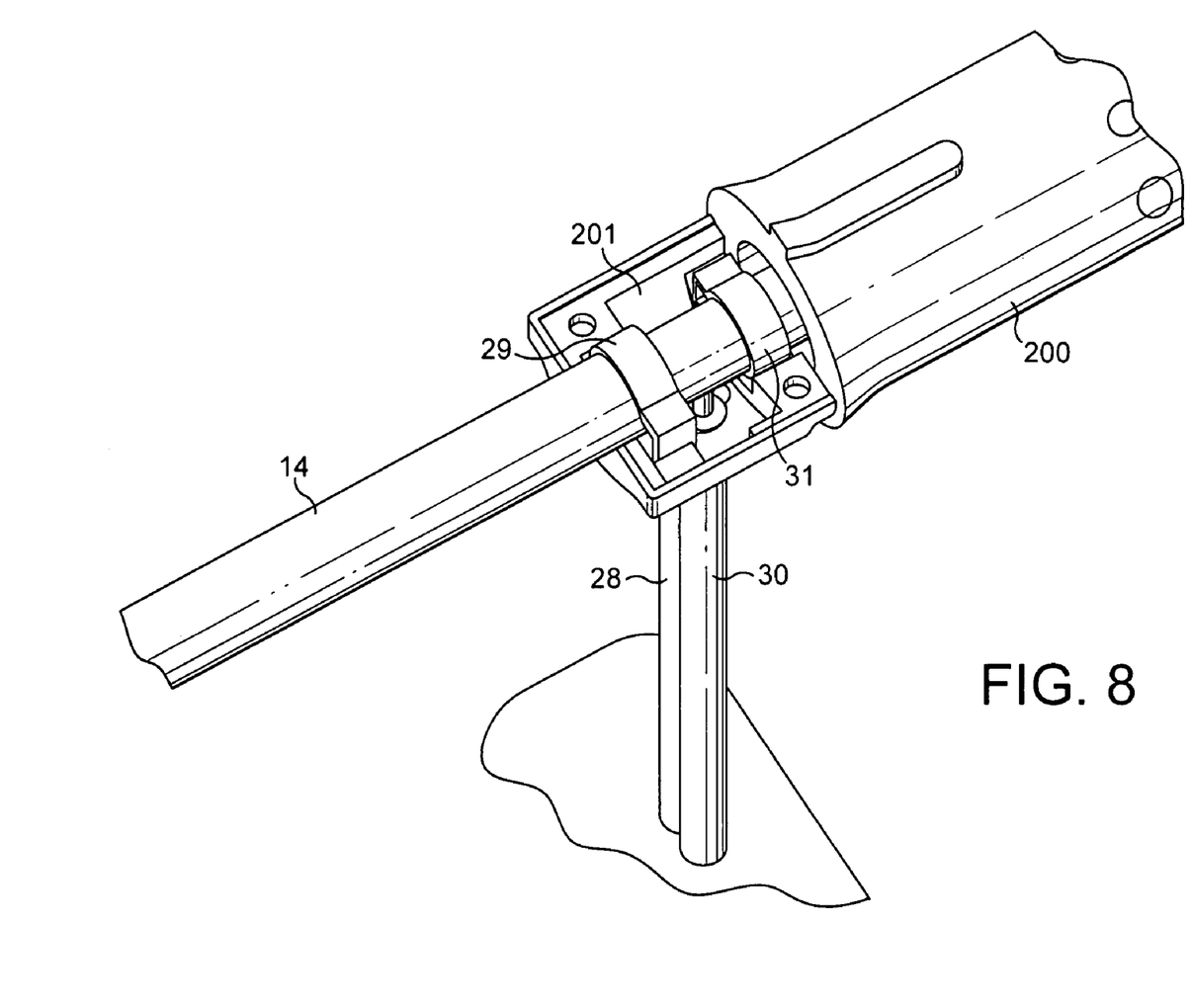
FIG. 8 is a schematic view, shown partly in section, of the proximal end of the probe of the surgical instrument of FIG. 1.

FIG. 8 shows how the intermediate tubular member 18 and the outer member 14 are connected to the electrosurgical generator 1. A first lead 28 supplies signals from one pole of the generator 1, and is connected to the outer tubular member 14 by means of clip assembly 29. A second lead 30 is connected to the other pole of the generator 1, and is in electrical communication with the intermediate tubular member 18 by means of second clip assembly 31. The clip assemblies are covered by a plastics casing 201, which is filled with epoxy potting compound to separate the first and second clip assemblies 29 and 31.

Figure 9:
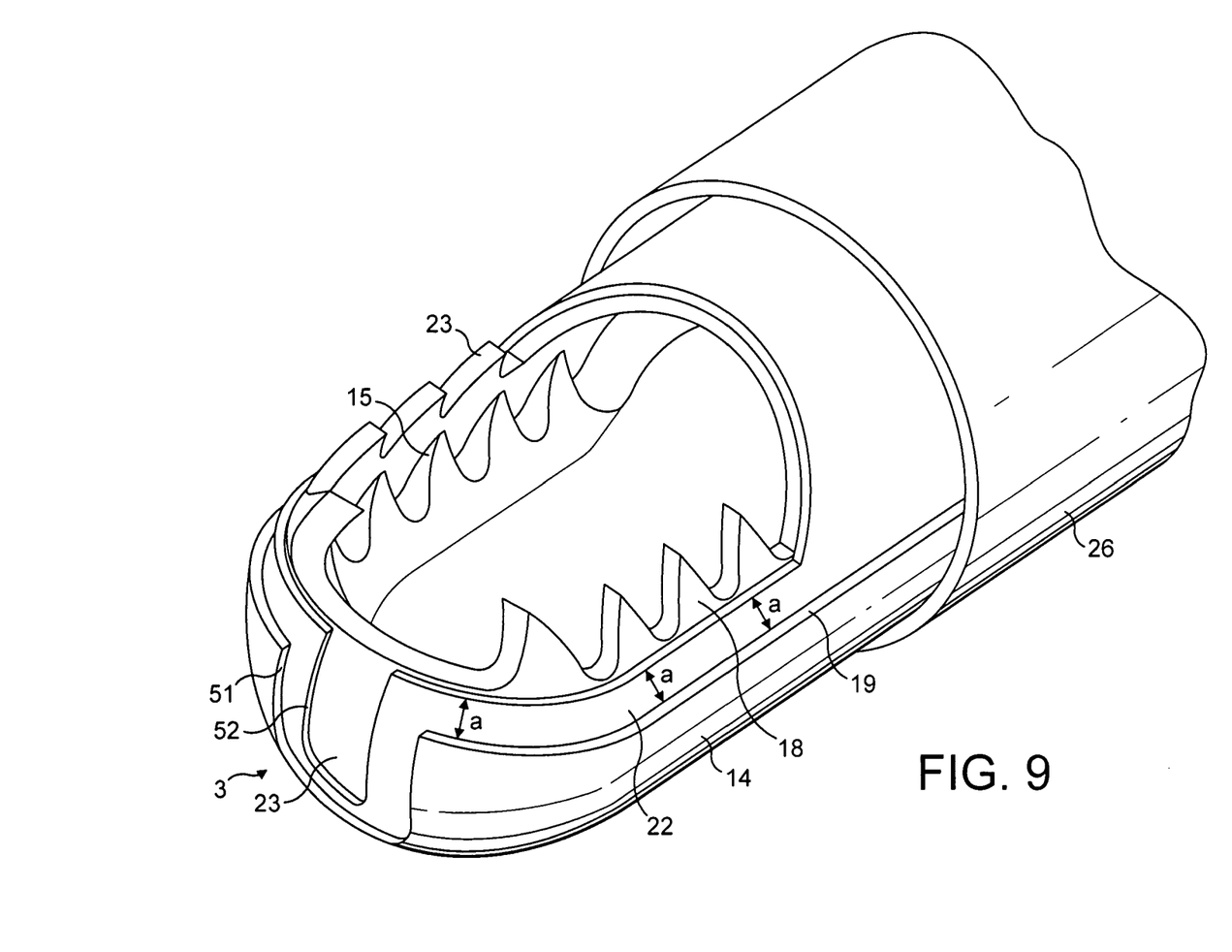
FIG. 9 is a schematic close-up view of an embodiment of the distal end of the probe of the instrument of FIG. 1.

The manufacture and use of the instrument will now be described, with particular reference to FIG. 9. The outer tube 14 and intermediate tube 18 are manufactured in a straight condition, and have manufacturing tolerances such that the distance "a" (see FIG. 9) between the two tubes at the distal end thereof are closely controlled. However, where an angled blade is required, the tubes 14 and 18 are subjected to a bending process, in which the tubes are bent at the curved portion 42. Without the provision of the weakened portion 43, the bending of the tubes would distort the distance between the tubes at the distal end of the instrument such that the separation therebetween would be less than the distance "a" in some locations and greater than the distance "a" in others. In particular, the bending of the tubes would cause the opening 19 in the outer tube 14 to become misaligned with the cutting window 16 in the intermediate member 18. The provision of the weakened section 43 prevents such misalignment from occurring.

In use of the instrument, when the cutting of tissue is required, the motor 5 is activated to rotate the inner tubular member 15, thereby causing the corresponding rotation of the cutting tool 17. The probe 3 is moved to engage tissue to be excised, and the tissue is drawn through the cutting windows 16 and 19 by the suction applied through the suction lumen 24 in the inner member 15. When the tissue enters the cutting window 16, it is severed by the rotation of the cutting tool 17 and the excised tissue is evacuated by the suction along the suction lumen 24.

When the coagulation of tissue is required, the electrosurgical generator 1 is actuated to supply bipolar coagulation signals to the intermediate tube 18 and outer tube 14, via the clip assemblies 29 and 31. Tissue coming into contact with the exposed portions 23 of the intermediate tube 18 will be coagulated by the electrosurgical signals from the generator 1. The exposed portions of the intermediate tube 18 firstly include the area around the cutting window 16, electrosurgical current flowing between the intermediate tubular member 18 and the outer member 14. Saline fed to the distal end of the probe from saline source 11 helps to carry the current between the members 18 and 14. The exposed portions of the intermediate tube 18 secondly include the area around slots 51 and 52. This allows coagulation of tissue at the distal tip of the probe 3, and also on the reverse face opposite the window 19. This allows the user to perform coagulation of tissue (for example to stem the flow of blood from bleeding tissue), without the user needing to stop the rotation of the cutting tool 17, by using areas of the instrument remote from the cutting window thereof.

Figure 10:
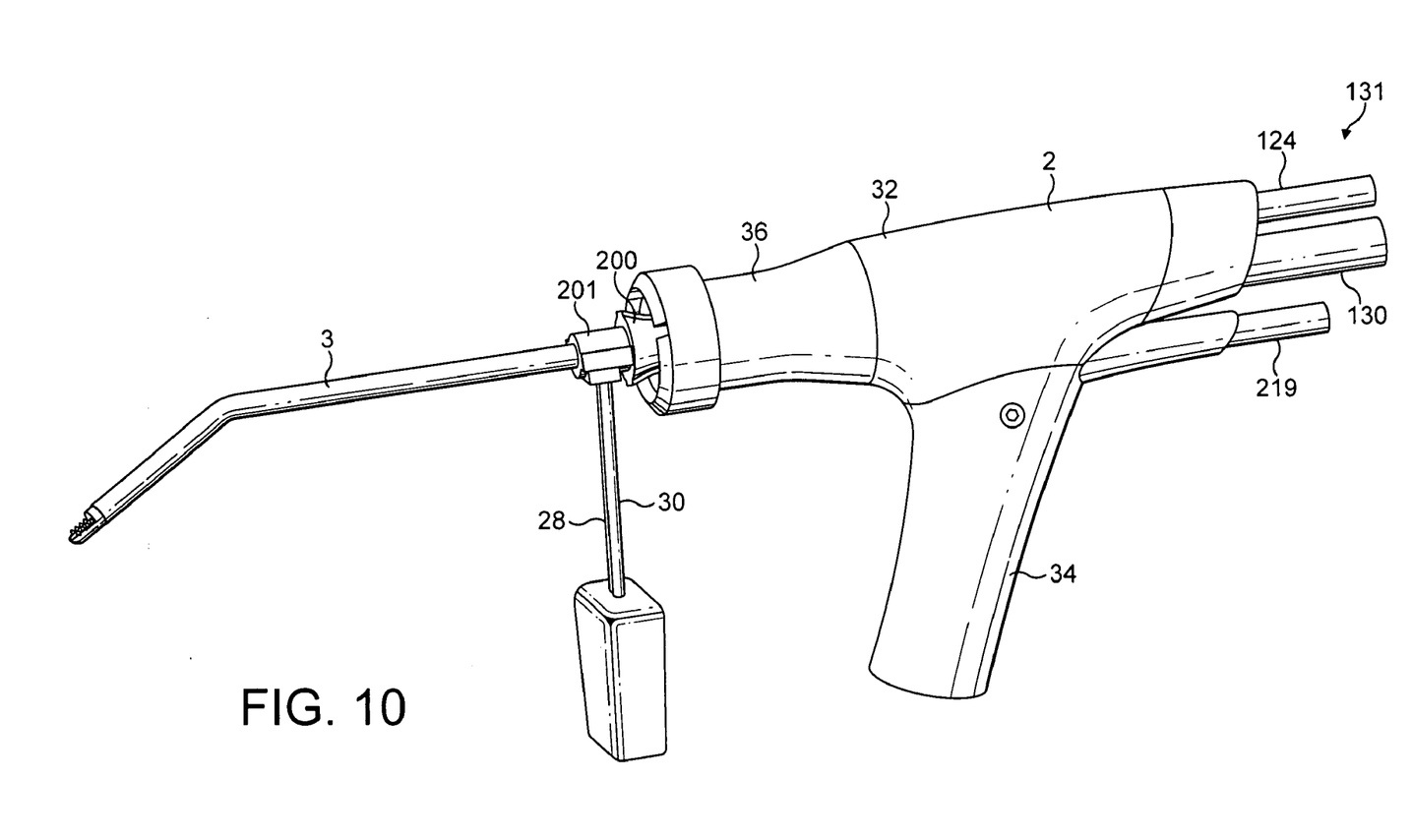
FIG. 10 is a side view of a surgical instrument in accordance with an alternative embodiment of the invention.

FIG. 10 shows an alternative embodiment of surgical device in which the handpiece 2 includes an upper portion 32 and a lower portion 34 defining a pistol grip arrangement. The upper portion 32 extends generally parallel to the probe 3, while the lower portion 34 extends at an angle thereto. The probe 3 is attached to the upper portion of the handpiece 2 by means of a collet assembly 36. The motor 5 (not shown in FIG. 4) is located in the lower portion 34 of the handpiece, and is controlled by signals via control line 219. Fluid irrigation and suction are provided to the handpiece 2 via dual tubing 131, the fluid supply being via tube 124 and the suction supply via tube 130. The dual tubing 131 is attached to the handpiece 2 by means of a connector 112.

A swivel collet assembly 36 is provided at the front end of the upper portion 32 of the handle 2. Disposing the collet assembly 36 at this location enables an operator, such as a surgeon, holding the handle 2 in a pistol grip manner, to touch and rotate the assembly collet 36 or a portion thereof with the tip of at least one of the surgeon's fingers. Rotating at least a portion of the collet assembly 36 in this manner enables the cutting window of the probe 3 to rotate, thereby orienting the direction of the shaving and/or cutting of the desired bodily material.

It will be appreciated by those skilled in the art that the embodiments described above firstly provide both mechanical cutting of tissue and electrosurgical coagulation at substantially the same part of the instrument, thereby avoiding the need for the surgeon to move or otherwise reorient the instrument to change between cutting and coagulation. However, there is also provided the option for tissue coagulation at a portion of the instrument remote from the cutting window, to allow the user to be able to coagulate tissue without stopping the rotation of the cutting element.

The invention claimed is:

1. A blade assembly for a surgical instrument including;
   a) an intermediate hollow tube having a central passageway and a cutting window at a distal end thereof, the tube being substantially straight but having a portion designated for bending, the bend portion being located over a finite distance between its proximal end and the cutting window;
   b) an inner hollow tube rotatably mounted in the central passageway of the intermediate tube and providing a central suction lumen, the inner tube having a flexible portion corresponding to the bend portion of the intermediate tube;
   c) a cutting tool disposed at the distal end of the inner tube such that the cutting tool is accessible through the cutting window of the intermediate tube, the cutting tool including a cut-out defining a tissue-cutting edge;
   d) an outer tube disposed over the intermediate hollow tube and having an opening at its distal end so as to allow access to the cutting window of the intermediate tube, the outer tube having a weakened portion located between the proximal end of the tube and the distal opening therein, the weakened portion corresponding to the bend portion of the intermediate tube,
   wherein (1) the bend portion of the intermediate hollow tube and the weakened portion of the outer tube are configured to cooperate structurally such that the inter-relationship between the opening in the outer tube and the cutting window in the intermediate tube is substantially the same whether in a first condition in which the outer tube and intermediate tube are straight, or in a second condition in which the outer tube and intermediate tube are bent at the bend portion and weakened portion respectively, and (2) a spacing between the distal ends of each of the intermediate hollow tube and the outer tube is maintained when the surgical instrument is in either the first position or the second position.

2. A blade assembly according to claim 1 wherein the intermediate and outer tubes are both electrically conducting, and there is an electrically insulating layer disposed between the intermediate and outer tubes.

3. A blade assembly according to claim 2 wherein the electrically insulating layer is provided by means of an insulating material deposited on to the outer surface of the intermediate tube.

4. A blade assembly according to claim 1 wherein there are first and second contacts respectively associated with the outer and intermediate tubes for connecting the tubes to respective poles of an electrosurgical generator.

5. A blade assembly according to claim 1 wherein the weakened portion comprises a portion of the outer tubular member with one or more sections removed therefrom.

6. A blade assembly according to claim 5 wherein the weakened portion comprises a portion of the tubular member in the form of a mesh.

7. A blade assembly according to claim 5 wherein the weakened portion comprises a plurality of ring elements connected one to another by joining members.

8. A blade assembly according to claim 5 wherein the weakened portion comprises a portion of the wall of the tube in the form of a strip, with the remainder of the tubular member being removed.

9. A blade assembly according to claim 8 wherein the strip extends helically around the circumference of the tubular element.

10. A blade assembly according to claim 8 wherein the strip is a longitudinally extending strip.

11. A blade assembly according to claim 10 wherein the strip extends in the form of a parallel strip with straight sides.

12. A blade assembly according to claim 10 wherein the strip extends in the form of a zig-zag element.

13. A blade assembly according to claim 8 wherein the strip constitutes less than 50% of the circumference of the tubular member.

14. A blade assembly according to claim 13 wherein the strip constitutes less than 20% of the circumference of the tubular member.

15. A blade assembly according to claim 14 wherein the strip constitutes less than 10% of the circumference of the tubular member.

16. A curved blade assembly for a surgical instrument including;
   a) an intermediate hollow tube having a central passageway and a cutting window at a distal end thereof, the tube having a bend portion, the bend portion being located over a finite distance between its proximal end and the cutting window;
   b) an inner hollow tube rotatably mounted in the central passageway of the intermediate tube and providing a central suction lumen, the inner tube having a flexible portion corresponding to the bend portion of the intermediate tube;
   c) a cutting tool disposed at the distal end of the inner tube such that the cutting tool is accessible through the cutting window of the intermediate tube, the cutting tool including a cut-out defining a tissue-cutting edge;
   d) an outer tube disposed over the intermediate hollow tube and having an opening at its distal end so as to allow access to the cutting window of the intermediate tube, the outer tube having a weakened portion located between the proximal end of the tube and the distal opening therein, the weakened portion corresponding to the bend portion of the intermediate tube,
   wherein (1) the bend portion of the intermediate hollow tube and the weakened portion of the outer tube are configured to cooperate structurally such that the inter-relationship between the opening in the outer tube and the cutting window in the intermediate tube is substantially the same in its bent condition as it was before the bend was formed, and (2) a spacing between the distal ends of each of the intermediate hollow tube and the outer tube is maintained when the surgical is either in the its bent condition or before the bend was formed.

* * * * *